United States Patent
Michihata

(10) Patent No.: US 11,615,514 B2
(45) Date of Patent: Mar. 28, 2023

(54) MEDICAL IMAGE PROCESSING APPARATUS AND MEDICAL OBSERVATION SYSTEM

(71) Applicant: Sony Olympus Medical Solutions Inc., Tokyo (JP)

(72) Inventor: Taihei Michihata, Tokyo (JP)

(73) Assignee: SONY OLYMPUS MEDICAL SOLUTIONS INC., Tokyo (JP)

(*) Notice: Subject to any disclaimer, the term of this patent is extended or adjusted under 35 U.S.C. 154(b) by 170 days.

(21) Appl. No.: 17/129,941

(22) Filed: Dec. 22, 2020

(65) Prior Publication Data
US 2021/0264578 A1 Aug. 26, 2021

(30) Foreign Application Priority Data
Feb. 26, 2020 (JP) ............... JP2020-030465

(51) Int. Cl.
*G06T 5/00* (2006.01)
*G06T 1/20* (2006.01)
*G06T 5/50* (2006.01)
*A61B 1/04* (2006.01)
*G06T 7/00* (2017.01)
*G06V 10/141* (2022.01)
*A61B 1/00* (2006.01)

(52) U.S. Cl.
CPC ............. *G06T 5/009* (2013.01); *A61B 1/043* (2013.01); *G06T 1/20* (2013.01); *G06T 5/002* (2013.01); *G06T 5/50* (2013.01); *G06T 7/0012* (2013.01); *G06V 10/141* (2022.01); *A61B 1/0002* (2013.01); *G06T 2207/10064* (2013.01); *G06T 2207/30004* (2013.01)

(58) Field of Classification Search
CPC .......... G06T 5/009; G06T 1/20; G06T 5/002; G06T 5/50; G06T 7/0012; G06T 2207/10064; G06T 2207/30004; G06T 1/60; G06T 1/0007; G06T 2207/10036; A61B 1/043; A61B 1/0002; A61B 1/00006; A61B 1/0638; A61B 1/000095; G06V 10/141; G02B 5/208; G02B 23/24; G02B 7/36; H04N 5/332; H04N 9/04553; H04N 9/04557; H04N 9/04559
See application file for complete search history.

(56) References Cited

U.S. PATENT DOCUMENTS

2020/0397298 A1* 12/2020 Talbert ................ H04N 5/2352
2020/0400795 A1* 12/2020 Talbert ................... G06T 5/003

FOREIGN PATENT DOCUMENTS

WO WO-2019087557 A1 * 5/2019 ............... A61B 1/00

* cited by examiner

*Primary Examiner* — Jose L Couso
(74) *Attorney, Agent, or Firm* — Xsensus LLP

(57) ABSTRACT

A medical image processing apparatus includes: a first captured image acquisition unit configured to acquire a first captured image obtained by capturing light from an observation target irradiated with light in a first wavelength band, the observation target emitting fluorescence when irradiated with excitation light in a second wavelength band different from the first wavelength band; a second captured image acquisition unit configured to acquire a second captured image obtained by capturing the fluorescence from the observation target irradiated with the excitation light; a first image processor configured to execute image processing on the first captured image; and a second image processor configured to execute image processing including blurring processing of blurring an image on the second captured image.

20 Claims, 9 Drawing Sheets

MEDICAL IMAGE PROCESSING APPARATUS AND MEDICAL OBSERVATION SYSTEM

CROSS-REFERENCE TO RELATED APPLICATION

This application claims priority from Japanese Application No. 2020-030465, filed on Feb. 26, 2020, the contents of which are incorporated by reference herein in its entirety.

BACKGROUND

The present disclosure relates to a medical image processing apparatus and a medical observation system.

In the related art, there is known a medical image processing apparatus that acquires first and second captured images, respectively, and superimposes the corresponding pixels of the first and second captured images on each other to generate a superimposed image (see, for example, US 2014/276008 A).

Here, the first captured image is an image obtained by irradiating an observation target with light in a first wavelength band and capturing the light reflected by the observation target with an imaging element. In addition, the second captured image is an image obtained by irradiating an observation target with excitation light in a second wavelength band different from the first wavelength band and capturing infrared light (fluorescence) from the observation target excited by the excitation light with an imaging element.

SUMMARY

Meanwhile, the second captured image has a remarkably lower signal level than the first captured image since the infrared light (fluorescence) from the observation target is extremely small and the sensitivity of the imaging element in the wavelength band of the infrared light is also low. In addition, since the signal level is extremely low, the second captured image has a low signal-to-noise ratio (SN ratio) and becomes an image with a high noise level if a gain (analog gain or digital gain) used to control the brightness of the second captured image is increased. That is, it is difficult to say that the second captured image is an image suitable for observation.

Therefore, there is a demand for a technique capable of generating the image suitable for observation.

There is a need for a medical image processing apparatus and a medical observation system that are able to generate an image suitable for observation.

According to one aspect of the present disclosure, there is provided a medical image processing apparatus including: a first captured image acquisition unit configured to acquire a first captured image obtained by capturing light from an observation target irradiated with light in a first wavelength band, the observation target emitting fluorescence when irradiated with excitation light in a second wavelength band different from the first wavelength band; a second captured image acquisition unit configured to acquire a second captured image obtained by capturing the fluorescence from the observation target irradiated with the excitation light; a first image processor configured to execute image processing on the first captured image; and a second image processor configured to execute image processing including blurring processing of blurring an image on the second captured image.

DETAILED DESCRIPTION

Hereinafter, a mode (hereinafter, an embodiment) for carrying out the present disclosure will be described with reference to the drawings. Incidentally, the present disclosure is not limited to the embodiment to be described below. Further, the same parts are denoted by the same reference signs when the drawings are described.

Schematic Configuration of Medical Observation System

Figure 1:
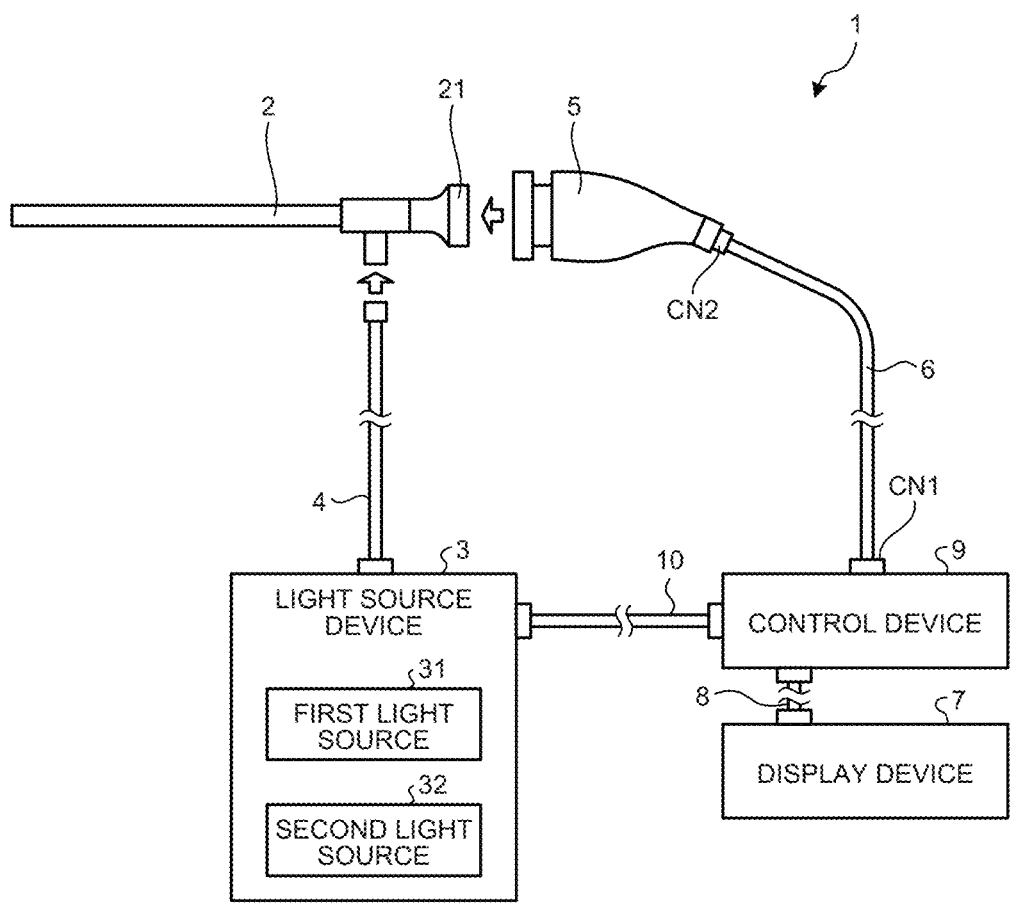
FIG. 1 is a diagram illustrating a configuration of a medical observation system according to an embodiment.

FIG. 1 is a diagram illustrating a configuration of a medical observation system 1 according to the embodiment.

The medical observation system 1 is a system used in the medical field to image (observe) an in-vivo body (observation target) as a subject. As illustrated in FIG. 1, the medical observation system 1 includes an insertion unit 2, a light source device 3, a light guide 4, a camera head 5, a first transmission cable 6, a display device 7, a second transmission cable 8, a control device 9, and a third transmission cable 10.

In the embodiment, the insertion unit 2 is configured using a rigid endoscope. That is, the insertion unit 2 has an elongated shape, which is hard as a whole or has a part being soft and the other part being hard, and is inserted into a living body. An optical system, which is configured using one or a plurality of lenses and collects light from a subject, is provided inside the insertion unit 2.

The light source device 3 is connected with one end of the light guide 4, and supplies light irradiating the inside of the living body to the one end of the light guide 4 under the control of the control device 9. As illustrated in FIG. 1, the light source device 3 includes a first light source 31 and a second light source 32.

The first light source 31 outputs (emits) light in a first wavelength band. In the embodiment, the first light source 31 is configured using a light emitting diode (LED) that emits white light (light in the first wavelength band).

The second light source 32 outputs (emits) excitation light in a second wavelength band different from the first wavelength band. In the embodiment, the second light source 32 is configured using a semiconductor laser that emits near-infrared excitation light (excitation light in the second wavelength band) in a near-infrared wavelength band.

The near-infrared excitation light emitted by the second light source 32 is excitation light that excites a fluorescent substance that emits light of indocyanine green or the like. In addition, when being excited by the near-infrared excitation light, the fluorescent substance that emits light of indocyanine green or the like emits fluorescence having a center wavelength on a longer wavelength side than a center wavelength of a wavelength band of the near-infrared excitation light. Incidentally, the wavelength band of the near-infrared excitation light and the wavelength band of the fluorescence may be set so as to partially overlap each other, or may be set so as not to overlap at all.

Further, the first light source 31 is driven in a normal observation mode under the control of the control device 9 in the light source device 3 according to the embodiment. That is, the light source device 3 emits normal light (white light) in the normal observation mode.

The normal observation mode corresponds to a first observation mode. On the other hand, in the light source device 3, the first light source 31 is driven in a first period and the second light source 32 is driven in a second period between the first and second periods that are alternately repeated in a fluorescence observation mode under the control of the control device 9. That is, in the fluorescence observation mode, the light source device 3 emits normal light (white light) in the first period and emits near-infrared excitation light in the second period. The fluorescence observation mode corresponds to a second observation mode.

Incidentally, the light source device 3 is configured as a separate body from the control device 9 in the embodiment, but the present disclosure is not limited thereto, and a configuration provided inside the control device 9 may be adopted.

The light guide 4 has one end detachably connected to the light source device 3 and the other end detachably connected to the insertion unit 2. Further, the light guide 4 transmits light (normal light or near-infrared excitation light) supplied from the light source device 3 from the one end to the other end and supplies the light to the insertion unit 2. When a living body is irradiated with normal light (white light), the normal light reflected in the living body is collected by the optical system in the insertion unit 2. Incidentally, the normal light collected by the optical system in the insertion unit 2 will be described as a first subject image for convenience of the description hereinafter. In addition, when a living body is irradiated with near-infrared excitation light, the near-infrared excitation light reflected in the living body and fluorescence, emitted from a fluorescent substance as the fluorescent substance that emits light of indocyanine green or the like accumulated in a lesion in the living body is excited, are collected by the optical system in the insertion unit 2. Incidentally, the near-infrared excitation light and fluorescence collected by the optical system in the insertion unit 2 will be referred to as a second subject image for convenience of the description hereinafter.

The camera head 5 corresponds to an imaging device. The camera head 5 is detachably connected to a proximal end (eyepiece 21 (FIG. 1)) of the insertion unit 2. Further, the camera head 5 captures the first subject image (normal light) and the second subject image (near-infrared excitation light and fluorescence) collected by the insertion unit 2 under the control of the control device 9, and outputs an image signal (RAW signal) obtained by the capturing.

Incidentally, a detailed configuration of the camera head 5 will be described later.

The first transmission cable 6 has one end detachably connected to the control device 9 via a connector CN1 (FIG. 1) and the other end detachably connected to the camera head 5 via a connector CN2 (FIG. 1). Further, the first transmission cable 6 transmits the image signal or the like output from the camera head 5 to the control device 9, and also transmits each of a control signal, a synchronization signal, a clock signal, power, and the like output from the control device 9 to the camera head 5.

Incidentally, in the transmission of the image signal or the like from the camera head 5 to the control device 9 via the first transmission cable 6, the image signal or the like may be transmitted as an optical signal or may be transmitted as an electrical signal. The same applies to the transmission of the control signal, the synchronization signal, and the clock from the control device 9 to the camera head 5 via the first transmission cable 6.

The display device 7 is configured using a display using a liquid crystal, an organic electro luminescence (EL), or the like, and displays an image based on a video signal from the control device 9 under the control of the control device 9.

The second transmission cable 8 has one end detachably connected to the display device 7 and the other end detachably connected to the control device 9. Further, the second transmission cable 8 transmits the video signal processed by the control device 9 to the display device 7.

The control device 9 corresponds to the medical image processing apparatus. The control device 9 is configured using a central processing unit (CPU), a field-programmable gate array (FPGA), or the like, and performs overall control of operations of the light source device 3, the camera head 5, and the display device 7.

Incidentally, a detailed configuration of the control device 9 will be described later.

The third transmission cable 10 has one end detachably connected to the light source device 3 and the other end detachably connected to the control device 9. Further, the third transmission cable 10 transmits the control signal from the control device 9 to the light source device 3.

Configuration of Camera Head

Next, the configuration of the camera head 5 will be described.

Figure 2:
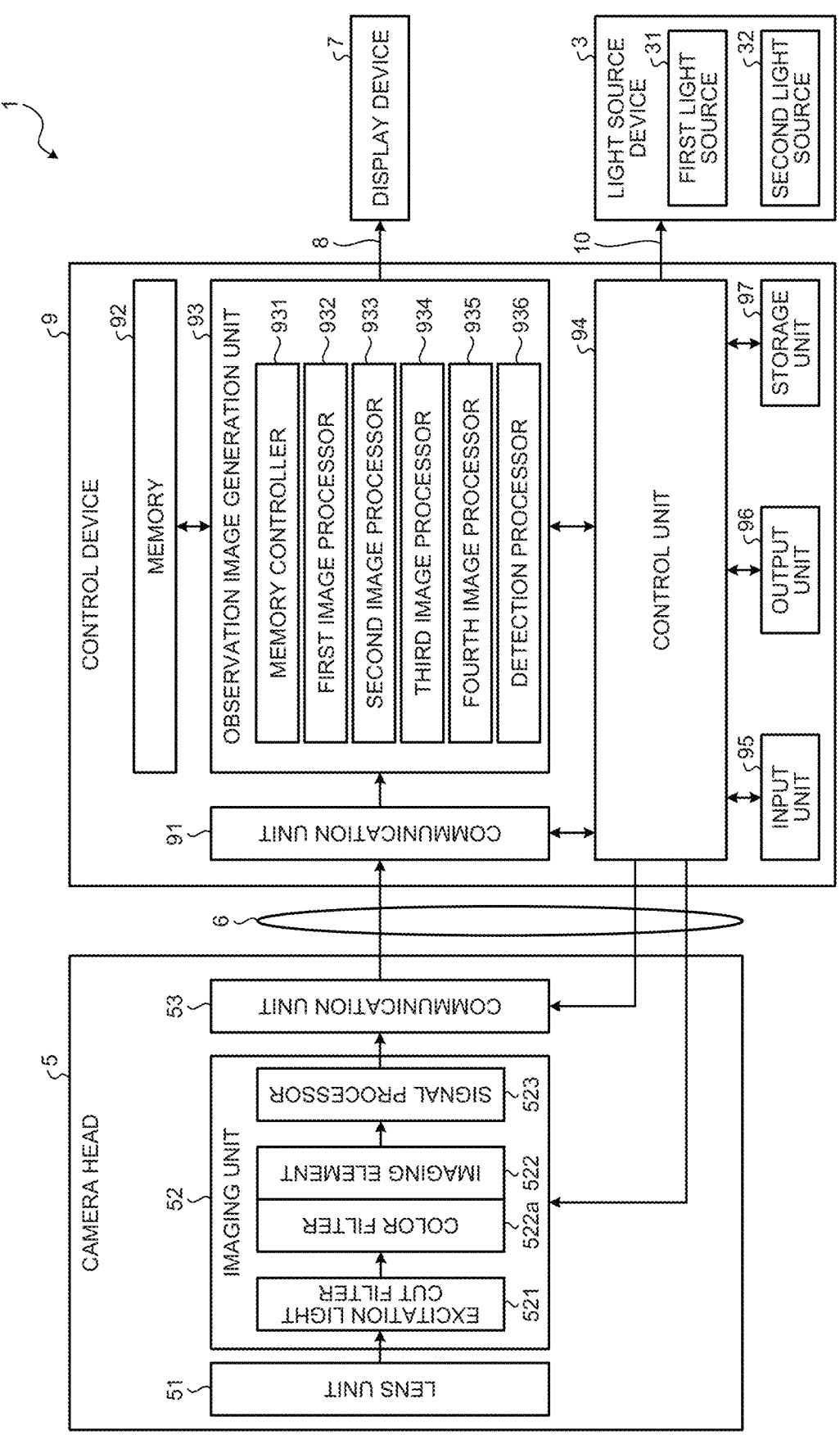
FIG. 2 is a block diagram illustrating a configuration of a camera head and a control device.

FIG. 2 is a block diagram illustrating the configurations of the camera head 5 and the control device 9.

Incidentally, FIG. 2 does not illustrate the connectors CN1 and CN2 between the control device 9 and the camera head 5, and the first transmission cable 6, a connector between the control device 9 and the display device 7, and the second transmission cable 8, and a connector between the control device 9 and the light source device 3, and the third transmission cable 10 for convenience of the description.

As illustrated in FIG. 2, the camera head 5 includes a lens unit 51, an imaging unit 52, and a communication unit 53.

The lens unit 51 is configured using one or a plurality of lenses, and forms the first subject image (normal light) and the second subject image (near-infrared excitation light and fluorescence) collected by the insertion unit 2 on an imaging surface of the imaging unit 52 (imaging element 522).

The imaging unit 52 captures the inside of a living body under the control of the control device 9. As illustrated in FIG. 2, the imaging unit 52 includes an excitation light cut filter 521, the imaging element 522, and a signal processor 523.

The excitation light cut filter 521 is provided between the lens unit 51 and the imaging element 522, and is configured using a band stop filter that removes a specific wavelength band. Incidentally, hereinafter, for convenience of the description, a wavelength band cut (removed) by the excitation light cut filter 521 will be referred to as a cut band, a wavelength band that is on a shorter wavelength side than the cut band and is transmitted through the excitation light cut filter 521 will be described as a short-wave-side transmission band, and a wavelength band that is on a longer wavelength side than the cut band and is transmitted through the excitation light cut filter 521 will be referred to as a long-wave-side transmission band.

Here, the cut band includes at least a partial wavelength band out of the wavelength band of the near-infrared excitation light. In the embodiment, the cut band includes a partial wavelength band of the wavelength band of the near-infrared excitation light. In addition, the long-wave-side transmission band includes a partial wavelength band of the wavelength band of the near-infrared excitation light and the wavelength band of fluorescence. Further, the short-wave-side transmission band includes a wavelength band (first wavelength band) of normal light (white light).

That is, the excitation light cut filter 521 passes the first subject image (normal light (white light)) directed from the lens unit 51 to the imaging element 522. On the other hand, the excitation light cut filter 521 passes a part of the near-infrared excitation light and the fluorescence regarding the second subject image (near-infrared excitation light and fluorescence) directed from the lens unit 51 to the imaging element 522.

The imaging element 522 is configured using a charge coupled device (CCD), a complementary metal oxide semiconductor (CMOS), or the like that receives light having transmitted through the excitation light cut filter 521 and converts the light into an electrical signal (analog signal).

Here, on the imaging surface (light receiving surface) of the imaging element 522, a color filter 522a (FIG. 2) in which three filter groups grouped in response to wavelength bands of the transmitted light (R (red), G (green), B (blue)) are arrayed in a predetermined format (for example, a Bayer array) is provided.

Specifically, the color filter 522a has an R filter group that mainly passes light in a wavelength band of R, a B filter group that mainly passes light in a wavelength band of B, and a G filter group that mainly passes light in a wavelength band of G.

Incidentally, the R, G, and B filter groups also pass near-infrared excitation light and fluorescence. Further, the imaging element 522 has sensitivity not only to light in the wavelength bands of R, G, and B but also to light in wavelength bands of the near-infrared excitation light and fluorescence.

Further, the imaging element 522 captures the first subject image (normal light) at a predetermined frame rate in the normal observation mode under the control of the control device 9. In addition, the imaging element 522 performs imaging in the fluorescence observation mode every first period and second period, which are alternately repeated, in synchronization with the light emission timing of the light source device 3 under the control of the control device 9.

Hereinafter, an image generated by capturing the first subject image (normal light) with the imaging element 522 will be referred to as a normal light image (corresponding to a first captured image) for convenience of the description. In addition, an image generated by capturing the second subject image (near-infrared excitation light and fluorescence) with the imaging element 522 will be referred to as a fluorescence image (corresponding to a second captured image). In addition, the normal light image and the fluorescence image are collectively referred to as a captured image.

The signal processor 523 performs signal processing on a captured image (analog signal) generated by the imaging element 522 and outputs the captured image (RAW signal (digital signal)) under the control of the control device 9.

For example, the signal processor 523 performs signal processing, such as processing of removing reset noise, processing of multiplying an analog gain for amplifying an analog signal, A/D conversion, and thinning processing, on the captured image (analog signal) generated by the imaging element 522.

Here, the thinning processing is processing of making the total number of pixels of a captured image a second number of pixels which is equal to or smaller than 1/N of (2/N in each of the vertical and horizontal directions) of a first number of pixels when the total number of pixels of the captured image generated by the imaging element 522 is set as the first number of pixels. That is, for example, a captured image having the number of pixels of 4K is converted into a captured image having the number of pixels of full high definition (HD) or lower by the thinning processing. Incidentally, in the thinning processing, the total number of pixels of the captured image may be set as the second number of pixels by deleting pixels of the captured image of which the total number of pixels is the first number of pixels at regular intervals, or the total number of pixels of the captured image may be set as the second number of pixels by adding adjacent pixels in the captured image of which the total number of pixels is the first number of pixels.

Figure 3:
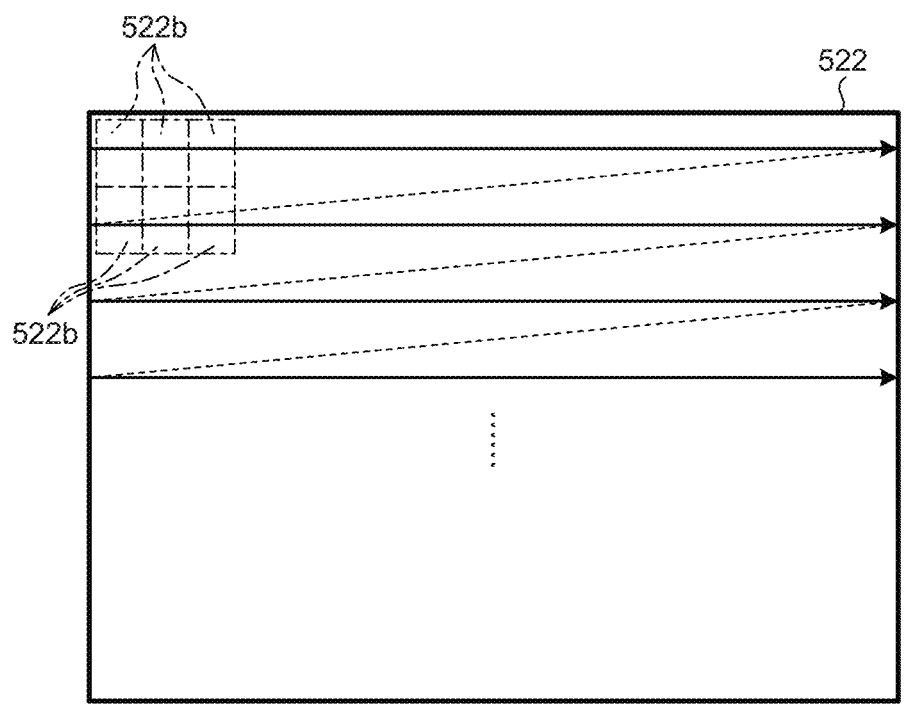
FIG. 3 is a view illustrating a captured image output from an imaging unit.

FIG. 3 is a view illustrating a captured image output from the imaging unit 52. Specifically, FIG. 3 is a view schematically illustrating the physical arrangement of each of pixels 522b in the imaging element 522.

Incidentally, FIG. 3 illustrates only some of the pixels 522b out of all the pixels in the imaging element 522 for convenience of the description.

The imaging unit 52 sequentially outputs captured images in raster units. Specifically, the respective pixels 522b are arranged in a matrix in the imaging element 522. Further, the imaging unit 52 outputs an image for one line from the respective pixels 522b in order from the pixel 522b arranged in the first column to the pixel 522b arranged in the last column among the respective pixels 522b in the first row as indicated by the arrows and broken lines in FIG. 3. Further, the imaging unit 52 continues the above processing until the final row, thereby outputting a captured image for one frame. When outputting a captured image for the next frame, the imaging unit 52 returns to the respective pixels 522b in the first row and performs the same processing as described above.

Incidentally, the raster output of the captured image when the above-described thinning processing is not performed has been described in the above description, but captured images after having been subjected to the thinning processing are sequentially output in raster units in the order indicated by the arrows and broken lines in FIG. 3.

The communication unit 53 functions as a transmitter that transmits captured images in raster units sequentially output from the imaging unit 52 to the control device 9 via the first transmission cable 6. The communication unit 53 is configured using, for example, a high-speed serial interface that performs communication of the captured image with the control device 9 at a transmission rate of 1 Gbps or more via the first transmission cable 6.

Configuration of Control Device

Next, the configuration of the control device 9 will be described with reference to FIG. 2.

As illustrated in FIG. 2, the control device 9 includes a communication unit 91, a memory 92, an observation image generation unit 93, a control unit 94, an input unit 95, an output unit 96, and a storage unit 97.

The communication unit 91 functions as a receiver that receives captured images in raster units which are sequentially output from the camera head 5 (communication unit 53) via the first transmission cable 6. The communication unit 91 is configured using, for example, a high-speed serial interface that performs communication of the captured image with the communication unit 53 at a transmission rate of 1 Gbps or more. That is, the communication unit 91 corresponds to a first captured image acquisition unit and a second captured image acquisition unit.

The memory 92 is configured using, for example, a dynamic random access memory (DRAM) or the like. This memory 92 temporarily stores a plurality of frames of captured images in raster units which are sequentially output from the camera head 5 (communication unit 53).

Under the control of the control unit 94, the observation image generation unit 93 processes captured images in raster units which have been sequentially output from the camera head 5 (communication unit 53) and received by the communication unit 91. As illustrated in FIG. 2, the observation image generation unit 93 includes a memory controller 931, first to fourth image processors 932 to 935, and a detection processor 936.

The memory controller 931 controls writing of an image to the memory 92 and reading of an image from the memory 92 under the control of the control unit 94. Incidentally, details of the functions of the memory controller 931 will be described in "Operation of Control Device" to be described later.

The first to fourth image processors 932 to 935 execute image processing in parallel on the respective input images under the control of the control unit 94. The first to fourth image processors 932 to 935 correspond to an image processor.

Figure 4:
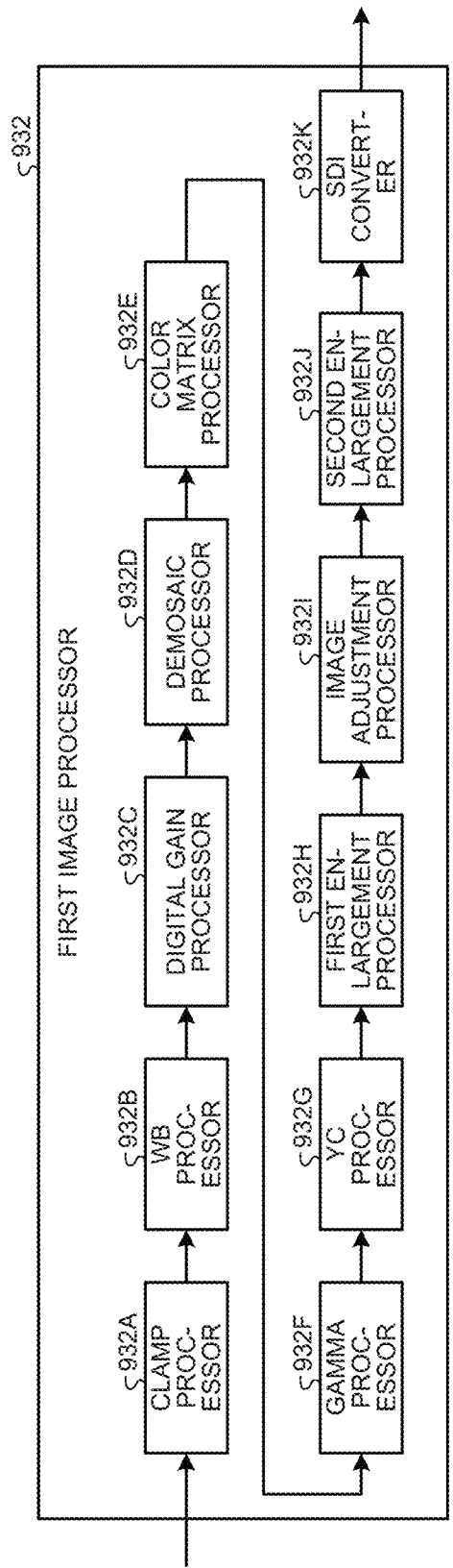
FIG. 4 is a block diagram illustrating a configuration of a first image processor.

FIG. 4 is a block diagram illustrating the configuration of the first image processor 932.

Incidentally, the configurations of the first to fourth image processors 932 to 935 are the same. Therefore, only the configuration of the first image processor 932 will be described hereinafter.

As illustrated in FIG. 4, the first image processor 932 includes a clamp processor 932A, a WB processor 932B, a digital gain processor 932C, a demosaic processor 932D, a color matrix processor 932E, a gamma processor 932F, a YC processor 932G, a first enlargement processor 932H, an image adjustment processor 932I, a second enlargement processor 932J, and a serial digital interface (SDI) converter 932K.

Here, images (images corresponding to the captured images (RAW data) output from the camera head 5) input to the first to the fourth image processors 932 to 935 include any component information (pixel data) of R, G, or B, which correspond to the respective filter groups of R, G, and B constituting the color filter 522a, per pixel. Hereinafter, for convenience of the description, the component information of R will be referred to as an r value, the component information of G will be referred to as a g value, and the component information of B will be referred to as a b value.

The clamp processor 932A executes clamp processing of fixing a black level on an input image.

The WB processor 932B performs WB processing (white balance adjustment processing) of multiplying each of an r value, a g value, and a b value in the image after having been subjected to the clamp processing by a specific gain.

The digital gain processor 932C executes digital gain processing of multiplying an r value, a g value, and a b value in the image after having been subjected to the WB processing by a digital gain and amplifying the r value, g value, and b value.

The demosaic processor 932D executes demosaic processing on the image after having been subjected to the digital gain processing to give pixel values (R (r value), G (g value), and B (b value)) of the r value, g value, and b value to each pixel by interpolation.

The color matrix processor 932E uses a color correction matrix to execute color matrix processing on the image after having been subjected to the demosaic processing to correct the pixel values (R, G, and B) per pixel to pixel values (Rm, Gm, and Bm).

The gamma processor 932F executes gamma processing (γ correction) on the image after having been subjected to the color matrix processing.

The YC processor 932G executes YC conversion that converts an image after having been subjected to the gamma processing into a luminance signal and a color difference signal (Y and $C_B/C_R$ signals).

The first enlargement processor 932H executes first enlargement processing (electronic zooming) on the image after having been subjected to the YC conversion.

The image adjustment processor 932I executes image adjustment processing on the image after having been subjected to the first enlargement processing (electronic zooming). Here, the image adjustment processor 932I is configured using a known filter, and has a function of executing image enhancement processing to enhance an image and a function to reversely execute blurring processing to blur an image (function such as a low-pass filter) by changing parameters. Incidentally, details of the functions of the image adjustment processor 932I will be described in "Regarding First and Second Image Processing" to be described later.

The second enlargement processor 932J executes second enlargement processing (electronic zooming) on the image after having been subjected to the image adjustment processing.

The SDI converter 932K executes SDI conversion on the image after having been subjected to the second enlargement processing (electronic zooming).

Further, the image from each of the SDI converters 932K in the first to fourth image processors 932 to 935 are output to the display device 7 as a first video signal or a second video signal to be described later via the second transmission cable 8.

The detection processor 936 executes detection processing based on the image after having been subjected to various types of image processing in the first to fourth image processors 932 to 935.

Specifically, the detection processor 936 executes detection of contrast and a frequency component of an image in detection area based on pixel information (for example, a luminance signal (Y signal)) per pixel in the detection area, which is at least a part of the entire image area of the captured image for one frame, detection of an average brightness value and the maximum and minimum pixels in the detection area using a filter or the like, comparison determination with a threshold, and detection of a histogram or the like (detection processing). Further, the detection processor 936 outputs detection information (contrast, frequency component, average brightness value, maximum and minimum pixels, histogram, and the like), obtained by the detection processing, to the control unit 94.

The control unit 94 is configured using, for example, a CPU, an FPGA, or the like, and outputs a control signal via the first to third transmission cables 6, 8, and 10 to control the operations of the light source device 3, the camera head 5, and the display device 7 and control the operation of the entire control device 9. Incidentally, the function of the control unit 94 will be described in "Operation of Control Device" to be described later.

The input unit 95 is configured using an operation device such as a mouse, a keyboard, and a touch panel, and receives a user operation by a user such as a doctor. Further, the input unit 95 outputs an operation signal according to the user operation to the control unit 94.

The output unit 96 is configured using a speaker, a printer, or the like, and outputs various types of information.

The storage unit 97 stores a program to be executed by the control unit 94, information necessary for processing of the control unit 94, and the like.

Operation of Control Device

Next, the operation of the above-described control device 9 will be described.

Figure 5:
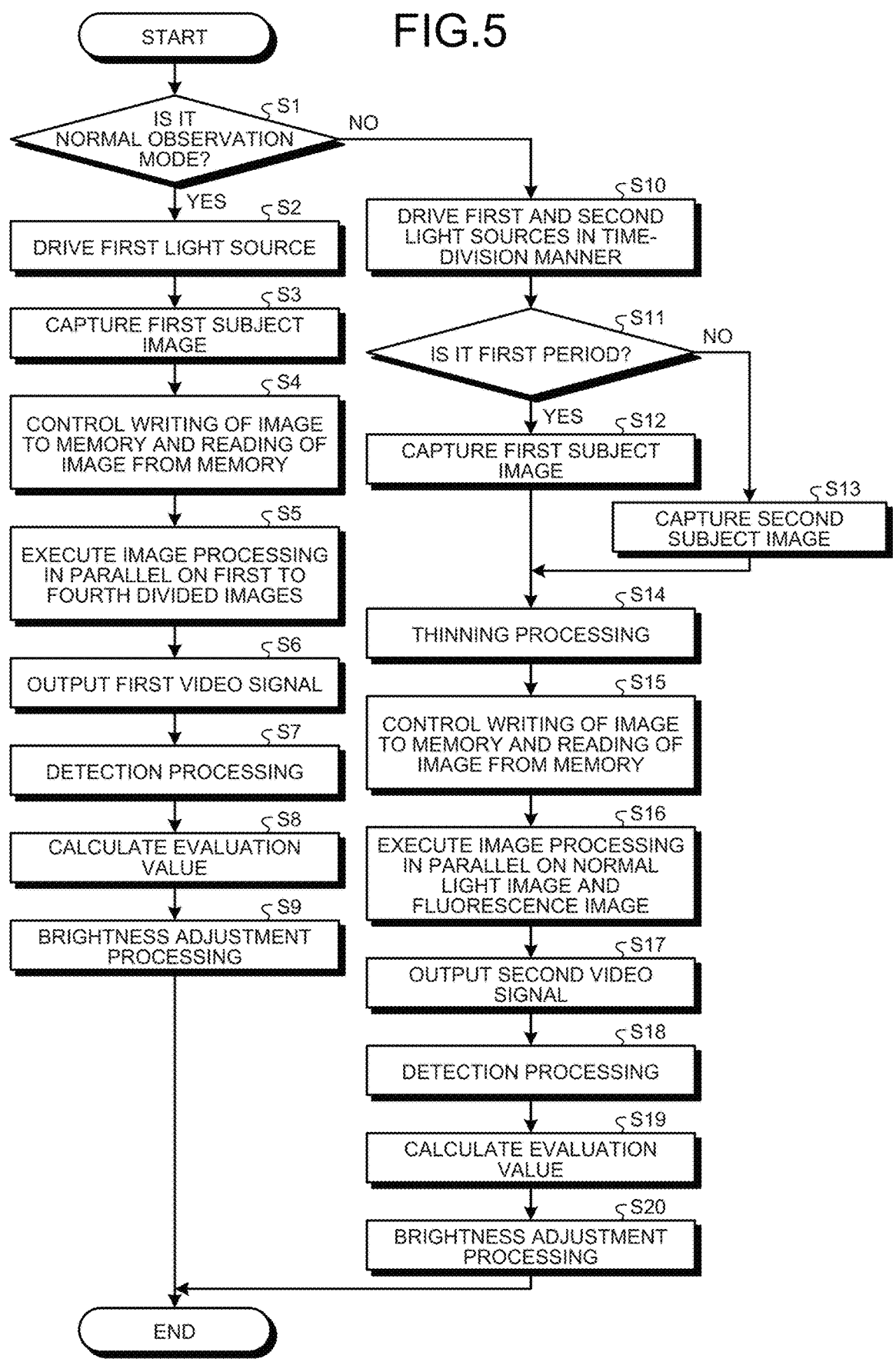
FIG. 5 is a flowchart illustrating an operation of the control device.

FIG. 5 is a flowchart illustrating the operation of the control device 9.

Incidentally, hereinafter, it is assumed that the imaging element 522 is an imaging element that generates a captured image having the number of pixels of 4K. In addition, it is assumed that the maximum amount of data that may be processed by the first image processor 932 is the amount of data of an image having the number of pixels of full HD. The same applies to the other second to fourth image processors 933 to 935.

First, the control unit 94 determines whether a current mode of the control device 9 is the normal observation mode (Step S1).

Incidentally, the mode of the control device 9 may be switched by the control unit 94. Specifically, the control unit 94 switches the mode of the control device 9 to the normal observation mode or the fluorescence observation mode in response to the user operation on the input unit 95 by the user such as a doctor. That is, the control unit 94 corresponds to a mode switching unit.

When determining that the current mode is the normal observation mode (Step S1: Yes), the control unit 94 drives the first light source 31 (Step S2). That is, the inside of the living body is irradiated with the normal light (white light).

After Step S2, the control unit 94 causes the imaging element 522 to capture the first subject image (normal light) at a predetermined frame rate (Step S3). Further, the imaging unit 52 sequentially outputs normal light images having the number of pixels of 4K in raster units.

After Step S3, the memory controller 931 controls writing of an image to the memory 92 and reading of an image from the memory 92 (Step S4).

Figure 6:
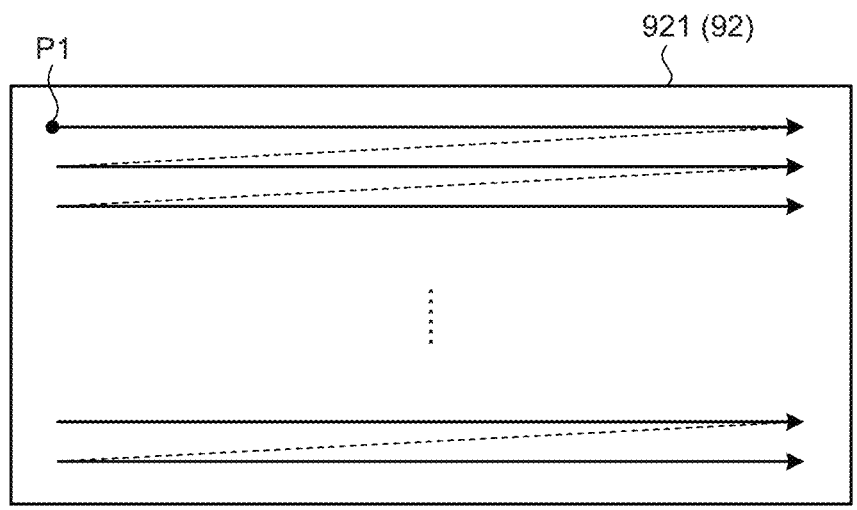
FIG. 6 is a view illustrating an operation of a memory controller in a normal observation mode.
Figure 7:
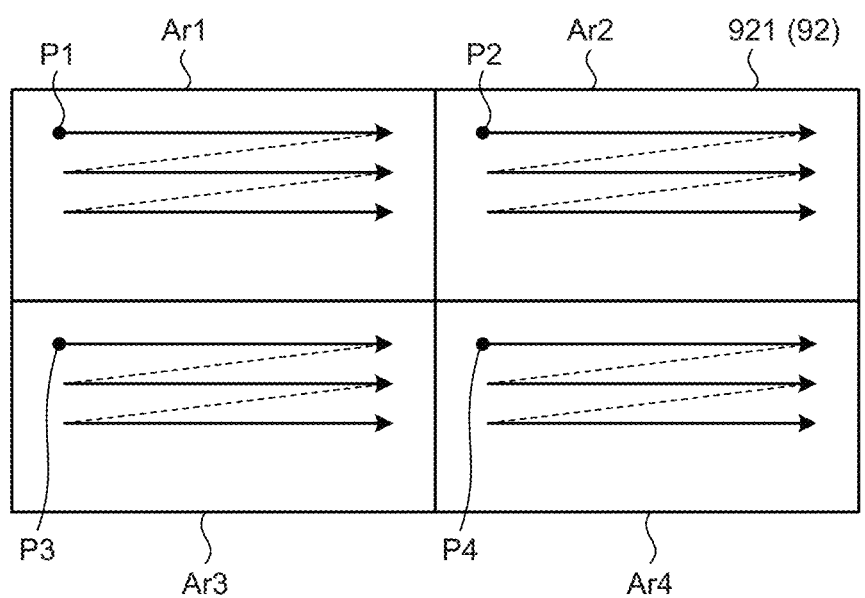
FIG. 7 is a view illustrating the operation of the memory controller in the normal observation mode.

FIGS. 6 and 7 are views illustrating the operation of the memory controller 931 in the normal observation mode. Specifically, FIG. 6 is a view illustrating writing of a normal light image to the memory 92. FIG. 7 is a view illustrating reading of a normal light image from the memory 92. Incidentally, FIGS. 6 and 7 schematically illustrate a specific bank 921 among a plurality of banks in the memory 92. The bank 921 corresponds to a first memory area, and has a memory capacity corresponding to the amount of data of an image having the number of pixels of 4K in the embodiment.

In addition, in FIG. 7, the entire area in the bank 921 is evenly divided into four first to fourth divided areas Ar1 to Ar4 in a crossed square shape. That is, the first to fourth divided areas Ar1 to Ar4 have a memory capacity corresponding to the amount of data of an image having the number of pixels of full HD in the embodiment.

Specifically, the memory controller 931 sequentially writes the normal light images (the number of pixels: 4K), which have been sequentially output from the imaging unit 52 as indicated by arrows and broken lines in FIG. 6 and received by the communication unit 91, to the bank 921 per line. Incidentally, one arrow illustrated in FIG. 6 indicates an image for one line in a normal light image (the number of pixels: 4K).

In addition, the memory controller 931 reads images written in the first to fourth divided areas Ar1 to Ar4 sequentially from first to fourth storage positions P1 to P4 per line as indicated by arrows and dashed lines in FIG. 7 almost at the same timing when writing the normal light image for one frame (the number of pixels: 4K) to the fourth storage position P4 (FIG. 7).

Incidentally, the image written in the first divided area Ar1 (hereinafter referred to as a first divided image) is an image of a rectangular area including an upper left corner position in the normal light image. Further, pixel data stored in the first storage position P1 is pixel data of a pixel at an upper left corner position in the first divided image. In addition, the image written in the second divided area Ar2 (hereinafter referred to as a second divided image) is an image of a rectangular area including an upper right corner position in the normal light image. Further, pixel data stored in the second storage position P2 is pixel data of a pixel at an upper left corner position in the second divided image. Further, the image written in the third divided area Ar3 (hereinafter referred to as a third divided image) is an image of a rectangular area including a lower left corner position in the normal light image. Further, pixel data stored in the third storage position P3 is pixel data of a pixel at an upper left corner position in the third divided image. In addition, the image written in the fourth divided area Ar4 (hereinafter referred to as a fourth divided image) is an image of a rectangular area including a lower right corner position in the normal light image. Further, pixel data stored in the fourth storage position P4 is pixel data of a pixel at an upper left corner position in the fourth divided image.

The first to fourth divided images described above are images obtained by evenly dividing the normal light image having the number of pixels of the number of pixels of 4K into four images, and thus, are images having the number of pixels of full HD.

Further, the read first to fourth divided images (the number of pixels: full HD) are sequentially input to the first to fourth image processors 932 to 935, respectively, per line. Incidentally, one arrow illustrated in FIG. 7 indicates an image for one line in the first to fourth divided images (the number of pixels: full HD).

After Step S4, the first to fourth image processors 932 to 935 execute image processing in parallel on the input first to fourth divided images (the number of pixels: full HD) (Step S5). Here, the first to fourth image processors 932 to 935 execute the first image processing on each of the input first to fourth divided images (the number of pixels: full HD). Incidentally, the first image processing will be described in "Regarding First and Second Image Processing" to be described later.

After Step S5, the observation image generation unit 93 outputs the first video signal, configured to display a normal light image (the number of pixels: 4K), obtained by combining the first to fourth divided images after having been subjected to the first image processing, to the display device 7 via the second transmission cable 8 (Step S6). As a result, the display device 7 displays the normal light image (the number of pixels: 4K) based on the first video signal.

After Step S6, the detection processor 936 executes detection processing based on pixel information for each pixel in a specific detection area out of the entire image area of the normal light image (the number of pixels: 4K) obtained by combining the first to fourth divided images after having been subjected to the first image processing in Step S5 (Step S7). Examples of the detection area may include an area including an image center in the normal light image (the number of pixels: 4K). Further, the detection processor 936 outputs detection information obtained by the detection processing to the control unit 94.

After Step S7, the control unit 94 calculates an evaluation value, configured to change a brightness of the image in the detection area to a reference brightness (change the detection information (average brightness value) to a reference average brightness value) based on the detection information (average brightness value) (Step S8). That is, the control unit 94 corresponds to an evaluation value calculator.

Here, examples of the evaluation value may include an exposure time of each pixel in the imaging element 522, an analog gain multiplied by the signal processor 523, a digital gain multiplied by the digital gain processor 932C, and the amount of normal light (white light) supplied by the first light source 31.

After Step S8, the control unit 94 executes brightness adjustment processing of adjusting the brightness of the image in the detection area to the reference brightness (Step S9).

Specifically, when the evaluation value calculated in Step S8 is the "exposure time", the control unit 94 outputs a control signal to the imaging unit 52 and sets the exposure time of each pixel of the imaging element 522 as the evaluation value. In addition, when the evaluation value calculated in Step S8 is the "analog gain", the control unit 94 outputs a control signal to the imaging unit 52 and sets the analog gain multiplied by the signal processor 523 as the evaluation value. Further, when the evaluation value calculated in Step S8 is the "digital gain", the control unit 94 outputs a control signal to the observation image generation unit 93 and sets the digital gain multiplied by each digital gain processor 932C in each of the first to fourth image processors 932 to 935 as the evaluation value. In addition, when the evaluation value calculated in Step S8 is the "amount of normal light (white light)", the control unit 94 outputs a control signal to the light source device 3 and sets the amount of normal light (white light) supplied by the first light source 31 as the evaluation value.

When returning to Step S1 and determining that the current mode is the fluorescence observation mode (Step S1: No), the control unit 94 drives the first and second light sources 31 and 32 in a time-division manner (Step S10). Specifically, in Step S10, the control unit 94 causes the first light source 31 to emit light in the first period and causes the second light source 32 to emit light in the second period between the first and second periods, which are alternately repeated, based on a synchronization signal.

After Step S10, the control unit 94 causes the imaging unit 52 to capture the first and second subject images in the first and second periods, respectively, in synchronization with the light emission timings of the first and second light sources 31 and 32 based on the synchronization signal (Steps S11 to S14). That is, in the first period (Step S11: Yes), in other words, when the inside of the living body is irradiated with the normal light (white light), the imaging element 522 captures the first subject image (normal light) to generate the normal light image (Step S12). On the other hand, in the second period (Step S11: No), in other words, when the inside of the living body is irradiated with the near-infrared excitation light, the imaging element 522 captures the second subject image (near-infrared excitation light and fluorescence) to generate the fluorescence image (Step S13). In addition, the signal processor 523 executes thinning processing (Step S14). By the thinning processing, the normal light image and the fluorescence image having the number of pixels of 4K are converted into the normal light image and the fluorescence image having the number of pixels of full HD, respectively.

Further, the imaging unit 52 sequentially outputs the normal light images having the number of pixels of full HD obtained by capturing in the first period in raster units, and sequentially outputs the fluorescence images having the number of pixels of full HD obtained by capturing in the second period in raster units.

After Step S14, the memory controller 931 controls writing of an image to the memory 92 and reading of an image from the memory 92 (Step S15).

Figure 8A:
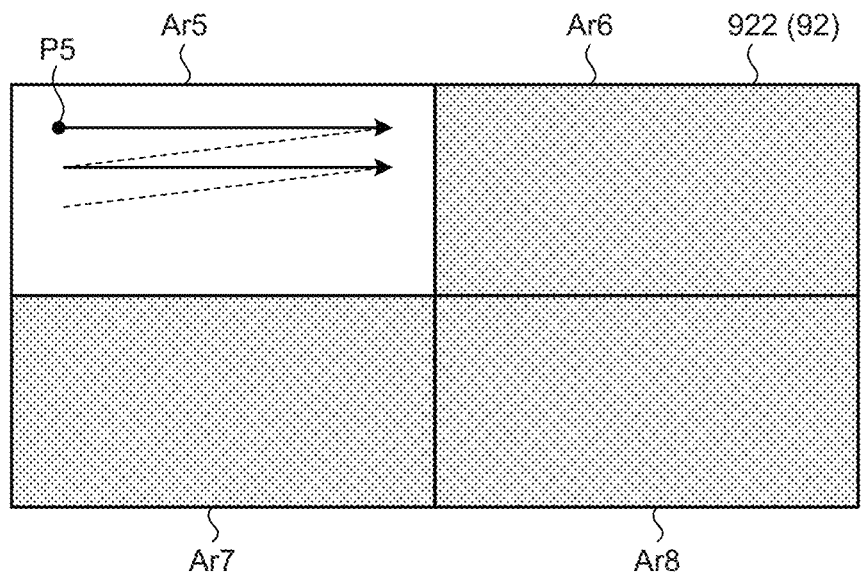
FIGS. 8A and 8B are views illustrating an operation of the memory controller in a fluorescence observation mode.
Figure 8B:
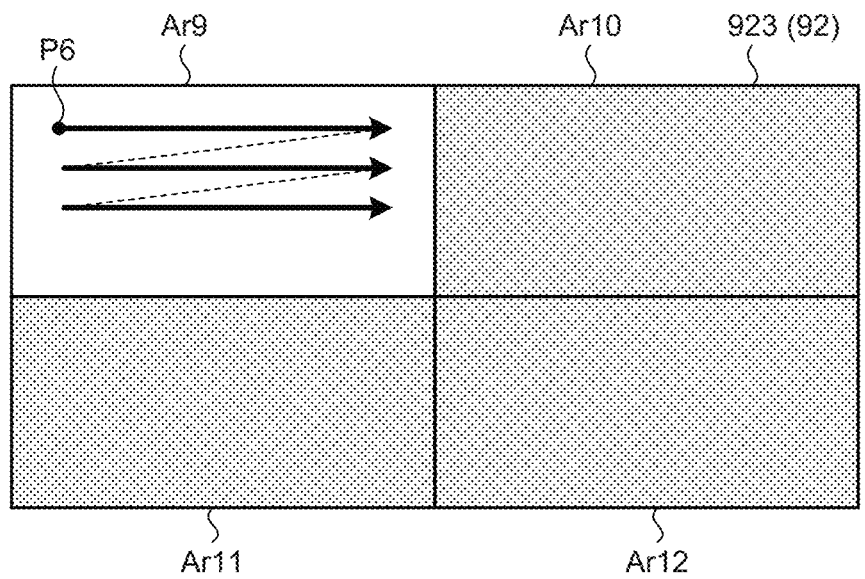
Figure 9A:
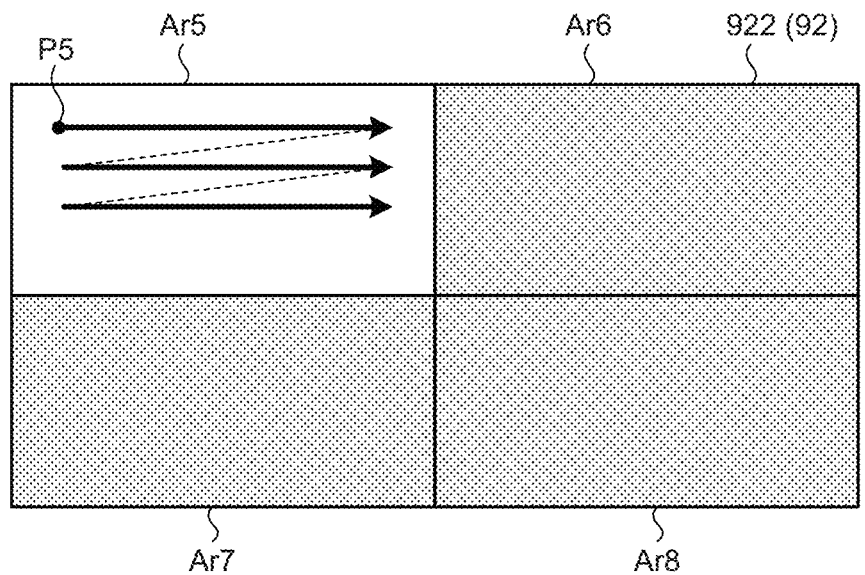
FIGS. 9A and 9B are views illustrating an operation of the memory controller in a fluorescence observation mode.
Figure 9B:
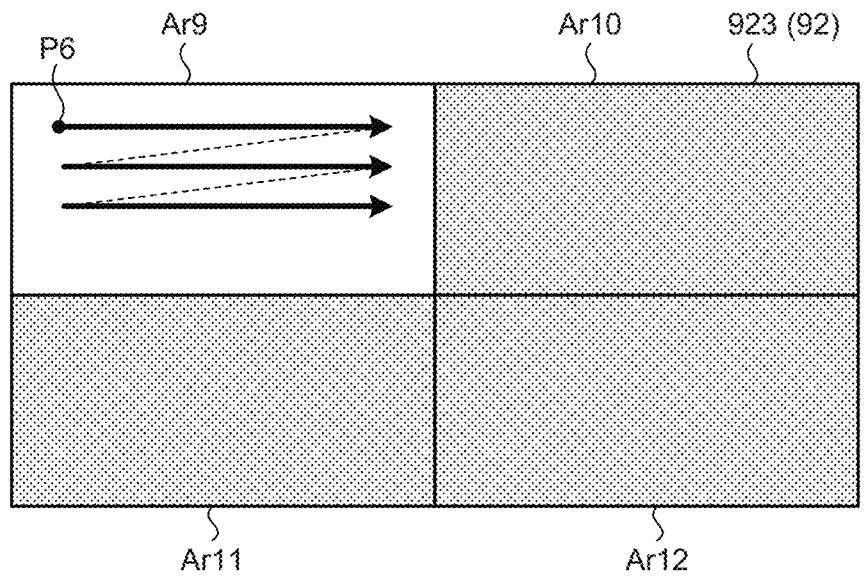

FIGS. 8A to 9B are views illustrating the operation of the memory controller 931 in the fluorescence observation mode. Specifically, FIG. 8A is a view illustrating writing of a normal light image to the memory 92. FIG. 8B is a view illustrating writing of a fluorescence image to the memory 92. FIG. 9A is a view illustrating reading of a normal light image from the memory 92. FIG. 9B is a view illustrating reading of a fluorescence image from the memory 92. Incidentally, FIGS. 8A to 9B schematically illustrate specific banks 922 and 923 among the plurality of banks in the memory 92. The banks 922 and 923 have the same memory capacity as the bank 921 (in the embodiment, the memory capacity corresponding to the amount of data of an image having the number of pixels of 4K). In addition, in FIGS. 8A to 9B, the entire area in the bank 922 is evenly divided into four fifth to eighth divided areas Ar5 to Ar8 in a crossed square shape, the entire area of bank 923 is evenly divided into four ninth to twelfth divided areas Ar9 to Ar12 in a crossed square shape. That is, the fifth to twelfth divided areas Ar5 to Ar12 have the same memory capacity as the first to fourth divided areas Ar1 to Ar4 (in the embodiment, the memory capacity corresponding to the amount of data of an image having the number of pixels of full HD). Incidentally, the fifth divided area Ar5 in the bank 922 corresponds to a second memory capacity. In addition, the ninth divided area Ar9 in the bank 923 corresponds to a third memory capacity.

Specifically, the memory controller 931 sequentially writes the normal light images (the number of pixels: full HD), which have been sequentially output from the imaging unit 52 as indicated by arrows and broken lines in FIG. 8A and received by the communication unit 91, to the fifth divided area Ar5 in the bank 922 per line. Incidentally, one arrow illustrated in FIG. 8A indicates an image for one line in the normal light image (the number of pixels: full HD). In addition, after writing the normal light image (the number of pixels: full HD) for one frame to the bank 922, the memory controller 931 sequentially writes the fluorescence light images (the number of pixels: full HD), which have been sequentially output from the imaging unit 52 as indicated by arrows and broken lines in FIG. 8B and received by the communication unit 91, to the ninth divided area Ar9 in the bank 923 per line. Incidentally, one arrow illustrated in FIG.

8B indicates an image for one line in the fluorescence image (the number of pixels: full HD).

In addition, the memory controller 931 sequentially reads the normal light images (the number of pixels: full HD) and fluorescence images (the number of pixels: full HD) respectively written in the fifth and ninth divided areas Ar5 and Ar9 from fifth and sixth storage positions P5 and P6 per line as indicated by arrows and dashed lines in FIGS. 9A and 9B almost at the same timing as the timing of starting to write the fluorescence image (the number of pixels: full HD) from the sixth storage position P6. Incidentally, one arrow illustrated in FIGS. 9A and 9B indicates an image for one line in the normal light image (the number of pixels: full HD) and the fluorescence image (the number of pixels: full HD). In addition, in FIGS. 8A to 9B, arrows at the same timing are illustrated as arrows having the same thickness. That is, the arrows illustrated in FIGS. 8B, 9A, and 9B have the same thickness, which is different from the thickness of the arrows illustrated in FIG. 8A. Here, pixel data stored in the fifth storage position P5 is pixel data of a pixel at an upper left corner position in the normal light image (the number of pixels: full HD). In addition, pixel data stored in the sixth storage position P6 is pixel data of a pixel at an upper left corner position in the fluorescence image (the number of pixels: full HD).

Further, the read normal light image (the number of pixels: full HD) and fluorescence image (the number of pixels: full HD) are sequentially input to the first and second image processors 932 and 933, respectively, per line. Incidentally, the third and fourth image processors 934 and 935 do not execute any processing in the fluorescence observation mode.

After Step S15, the first and second image processors 932 and 933 execute image processing in parallel on the input normal light image (the number of pixels: full HD) and fluorescence image (the number of pixels: full HD) (Step S16). Here, the first image processor 932 executes the first image processing on the input normal light image (the number of pixels: full HD). On the other hand, the second image processor 933 executes the second image processing on the input fluorescence image (the number of pixels: full HD). Incidentally, the first and second image processing will be described in "Regarding First and Second Image Processing" to be described later.

After Step S16, the observation image generation unit 93 outputs the second video signal, configured to display at least any image out of a normal light image after having been subjected to the first image processing, a fluorescence image after having been subjected to the second image processing, and a superimposed image in which corresponding pixels of the normal light image and the fluorescence image are superimposed on each other, to the display device 7 via the second transmission cable 8 (Step S17). As a result, the display device 7 displays an image (the number of pixels: 4K) based on the second video signal.

After Step S17, the detection processor 936 executes detection processing based on pixel information for each pixel in a specific detection area out of the entire image area of the normal light image (the number of pixels: full HD) after having been subjected to the first image processing in Step S16 (Step S18). Examples of the detection area may include an area including an image center in the normal light image (the number of pixels: full HD). Further, the detection processor 936 outputs detection information obtained by the detection processing to the control unit 94.

After Step S18, the control unit 94 calculates each of a normal light evaluation value a fluorescence evaluation value (Step S19). The normal light evaluation value and the fluorescence evaluation value correspond to an evaluation value.

Specifically, in Step S19, the control unit 94 calculates the normal light evaluation value, configured to change a brightness of the image in the detection area in the normal light image to a reference brightness (change the detection information (average brightness value) to a reference average brightness value) based on the detection information (average brightness value) similarly to Step S8. Here, there is a correlation between the normal light image and the fluorescence image obtained by capturing the same subject at substantially the same timing. Further, in Step S19, the control unit 94 uses the correlation to calculate the fluorescence evaluation value, configured to change a brightness of the fluorescence image to a reference brightness, from the above-described normal light evaluation value.

Here, examples of the normal light evaluation value may include an exposure time of each pixel in the imaging element 522 during a period of generating the normal light image, an analog gain multiplied by the signal processor 523 during the period of generating the normal light image, a digital gain multiplied by the digital gain processor 932C in the first image processing by the first image processor 932, and the amount of normal light (white light) supplied by the first light source 31 in the first period.

In addition, examples of the fluorescence evaluation value may include an exposure time of each pixel in the imaging element 522 during a period of generating the fluorescence image, an analog gain multiplied by the signal processor 523 during the period for generating the fluorescence image, a digital gain multiplied by the digital gain processor 932C in the second image processing by the second image processor 933, and the amount of near-infrared excitation light supplied by the second light source 32 in the second period.

After Step S19, the control unit 94 executes brightness adjustment processing of adjusting each brightness of the normal light image and the fluorescence image (Step S20).

Specifically, when the normal light evaluation value calculated in Step S19 is the "exposure time", the control unit 94 outputs a control signal to the imaging unit 52 and sets the exposure time of each pixel of the imaging element 522 during the period of generating the normal light image as the normal light evaluation value. In addition, when the normal light evaluation value calculated in Step S19 is the "analog gain", the control unit 94 outputs a control signal to the imaging unit 52 and sets the analog gain multiplied by the signal processor 523 during the period of generating the normal light image as the normal light evaluation value. Further, when the normal light evaluation value calculated in Step S19 is the "digital gain", the control unit 94 outputs a control signal to the observation image generation unit 93 and sets the digital gain multiplied by the digital gain processor 932C in the first image processing by the first image processor 932 as the normal light evaluation value. In addition, when the normal light evaluation value calculated in Step S19 is the "amount of normal light (white light)", the control unit 94 outputs a control signal to the light source device 3, and sets the amount of normal light (white light) supplied by the first light source 31 in the first period as the normal light evaluation value.

Similarly, when the fluorescence evaluation value calculated in Step S19 is the "exposure time", the control unit 94 outputs a control signal to the imaging unit 52 and sets the exposure time of each pixel of the imaging element 522 during the period of generating the fluorescence image as the fluorescence evaluation value. In addition, when the fluorescence evaluation value calculated in Step S19 is the "analog gain", the control unit 94 outputs a control signal to the imaging unit 52 and sets the analog gain multiplied by the signal processor 523 during the period of generating the fluorescence image as the fluorescence evaluation value. Further, when the fluorescence evaluation value calculated in Step S19 is the "digital gain", the control unit 94 outputs a control signal to the observation image generation unit 93 and sets the digital gain multiplied by the digital gain processor 932C in the second image processing by the second image processor 933 as the fluorescence evaluation value. In addition, when the fluorescence evaluation value calculated in Step S19 is the "amount of near-infrared excitation light", the control unit 94 outputs a control signal to the light source device 3, and sets the amount of near-infrared excitation light supplied by the second light source 32 in the second period as the fluorescence evaluation value.

Regarding First and Second Image Processing

In the first and second image processing, for example, the clamp processing, WB processing, the digital gain processing, the demosaic processing, the color matrix processing, the gamma processing, the YC processing, the first enlargement processing, and the image adjustment processing are executed as follows under the control of the control unit 94.

(1) Regarding Clamp Processing

In the first and second image processing, the same clamp processing is executed.

Incidentally, the second image processing may be provided with a function that enables a change of a value (black level) of the clamp processing.

With the configuration that enables the change of the value of the clamp processing as described above, it is possible to suppress dark noise that is hardly suppressed by the blurring processing alone. This function may be implemented by, for example, setting a desired threshold for a dark area noise value and performing control (providing a configuration) to change a value of the clamp processing in a direction of suppressing the dark noise when the dark area noise of an acquired fluorescence image exceeds the desired threshold.

(2) Regarding WB Processing

Between the first and second image processing, different gains are used in the WB processing.

Specifically, in the first image processing, an r value, a g value, and a b value in the first to fourth divided images (the number of pixels: full HD) or normal light image (the number of pixels: full HD) after having been subjected to the clamp processing are multiplied by three first gains, respectively, in the WB processing. The three first gains are gains configured to achieve white-balance among the r value, g value, and b value in a wavelength band of normal light (white light).

On the other hand, in the second image processing, an r value, a g value, and a b value in the fluorescence image (the number of pixels: full HD) after having been subjected to the clamp processing are multiplied by three second gains, respectively, in the WB processing. Here, the three second gains are substantially the same value since the sensitivity of the imaging element 522 to fluorescence is substantially the same for R, G, and B.

(3) Regarding Digital Gain Processing

In the first image processing, an r value, a g value, and a b value in the first to fourth divided images (the number of pixels: full HD) or normal light image (the number of pixels: full HD) after having been subjected to the WB processing are multiplied by the evaluation value (digital gain) calculated in Step S8 or the normal light evaluation value (digital gain) calculated in Step S19 in the digital gain processing.

On the other hand, in the second image processing, an r value, a g value, and a b value in the fluorescence image (the number of pixels: full HD) after having been subjected to the WB processing are multiplied by the fluorescence evaluation value (digital gain) calculated in Step S19 in the digital gain processing.

(4) Regarding Demosaic Processing

In the second image processing, the demosaic processing is not necessarily executed.

(5) Regarding Color Matrix Processing

In the first image processing, the color matrix processing is executed.

On the other hand, the color matrix processing is not executed in the second image processing since the fluorescence image has no color. Alternatively, the color matrix processing is executed in the second image processing using the color correction matrix that does not correct colors.

(6) Regarding Gamma Processing

In the second image processing, y correction with higher contrast as compared with the first image processing is executed.

(7) Regarding YC Conversion

In the second image processing, color difference values (Cb value and Cr value) are set to 0 (black and white image) in the luminance signal and the color difference signal after YC conversion. Alternatively, a slight color difference value may be added to add color in the second image processing.

(8) Regarding First Enlargement Processing

In the first and second image processing, the same electronic zooming magnification may be used in the first enlargement processing, or different electronic zooming magnifications may be used.

(9) Regarding Image Adjustment Processing

Figure 10A:
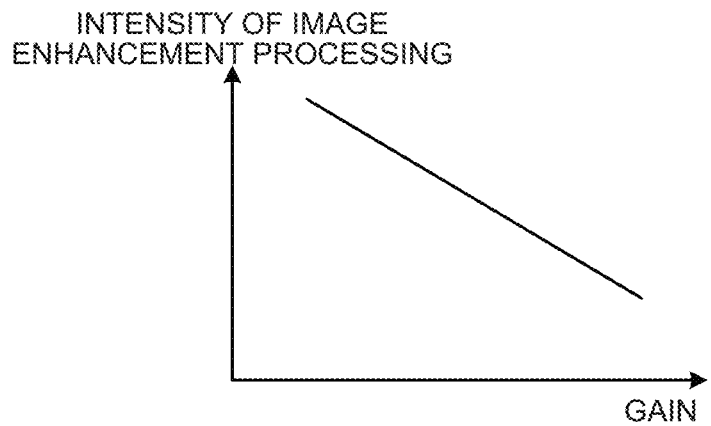
FIGS. 10A and 10B are views illustrating a difference in image adjustment processing in first and second image processing.
Figure 10B:
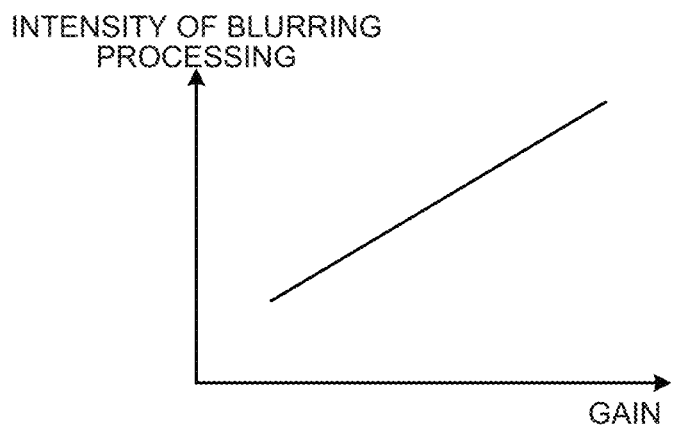

FIGS. 10A and 10B are views illustrating a difference in image adjustment processing in first and second image processing; and In the first image processing, image enhancement processing of enhancing an image is executed on the first to fourth divided images (the number of pixels: full HD) or normal light image (the number of pixels: full HD) after having been subjected to the first enlargement processing. Here, as illustrated in FIG. 10A, the intensity is decreased (the degree of enhancement is weakened) in the image enhancement processing as the evaluation value (analog gain or digital gain) calculated in Step S8 or the normal light evaluation value (analog gain or digital gain) calculated in Step S19 increases.

That is, in the first image processing, the intensity of the image enhancement processing is set to a third intensity when the evaluation value or the normal light evaluation value is a third evaluation value, and the intensity of the image enhancement processing is set to a fourth intensity lower than the third intensity when the evaluation value or the normal light evaluation value is a fourth evaluation value which is a value for increasing the brightness of the first to fourth divided images or the normal light image more than the third evaluation value.

On the other hand, in the second image processing, blurring processing of blurring an image is executed on the fluorescence image (the number of pixels: full HD) after having been subjected to the first enlargement processing. Here, as illustrated in FIG. 10B, the intensity is increased (the degree of blurring is strengthened) in the blurring processing as the fluorescence evaluation value (analog gain or digital gain) calculated in Step S19 increases.

That is, in the second image processing, the intensity of the blurring processing is set to a first intensity when the fluorescence evaluation value is a first evaluation value, and the intensity of the blurring processing is set to a second intensity higher than the first intensity when the fluorescence evaluation value is a second evaluation value which is a value for increasing the brightness of the fluorescence image more than the first evaluation value.

According to the embodiment described above, the following effects are achieved.

In the control device 9 according to the embodiment, the first and second image processors 932 and 933 are used to execute the image processing on each of the normal light image (the number of pixels: full HD) and the fluorescence image (the number of pixels: full HD). Here, the second image processor 933 executes image processing including the blurring processing of blurring the fluorescence image (the number of pixels: full HD). Therefore, with the control device 9 according to the embodiment, it is possible to effectively remove the noise of the fluorescence image (the number of pixels: full HD), which is an image having a high noise level, and generate an image suitable for observation.

In particular, the second image processor 933 increases the intensity of the blurring processing as the fluorescence evaluation value (analog gain or digital gain) increases. Therefore, it is possible to favorably generate the image suitable for observation without performing the blurring processing at the unnecessarily high intensity.

In addition, the first image processor 932 executes the image processing including the image enhancement processing of enhancing an image on the normal light image (the number of pixels: full HD). Therefore, for example, if the normal light image after having been subjected to the image processing and the fluorescence image after having been subjected to the image processing are displayed as, for example, a superimposed image, the image becomes an image more suitable for observation.

In particular, the first image processor 932 decreases the intensity of the image enhancement processing as the normal light evaluation value (analog gain or digital gain) increases. Therefore, it is possible to favorably generate the image suitable for observation without performing the image enhancement processing at the unnecessarily high intensity.

In addition, the control device 9 according to the embodiment executes the image processing in parallel on the first to fourth divided images using the first to fourth image processors 932 to 935 in the normal observation mode. On the other hand, the control device 9 executes the image processing in parallel on the normal light image and the fluorescence image using the first and second image processors 932 and 933 in the fluorescence observation mode.

That is, the image processor that executes the image processing in parallel on the first to fourth divided images and the image processor that executes the image processing in parallel on the normal light image and the fluorescence image may be configured as a shared image processor. Therefore, it is possible to generate an image suitable for observation without increasing the circuit scale.

Other Embodiments

The mode for carrying out the present disclosure have been described hereinbefore. However, the present disclosure is not limited only to the embodiment described above.

Figure 11:
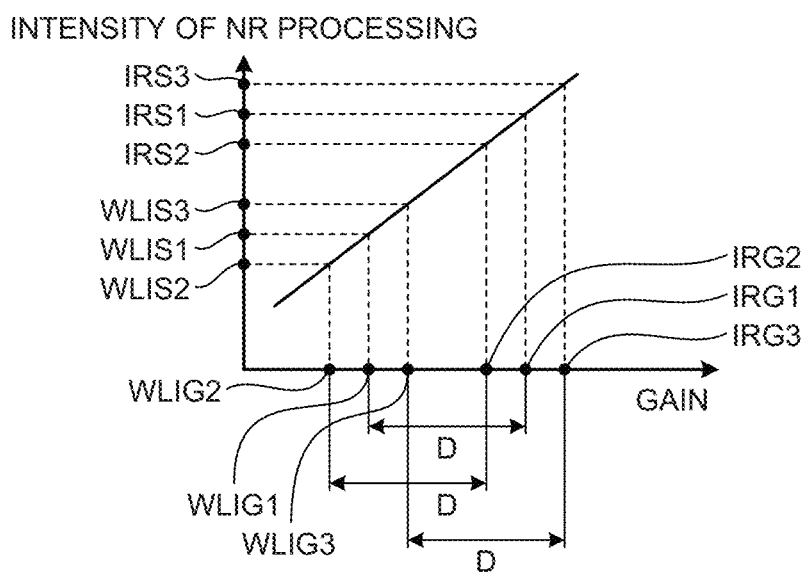
FIG. 11 is a graph illustrating a modification of the embodiment.

FIG. 11 is a graph illustrating a modification of the embodiment.

Noise reduction (NR) processing of applying a time filter or a spatial filter to remove noise in an image may be added to the first and second image processing executed by the first to fourth image processors 932 to 935 according to the above-described embodiment. At this time, as illustrated in FIG. 11, a correlation between an intensity and a gain (analog gain or digital gain) of the NR processing is used to adjust the intensity of the NR processing such that a normal light evaluation value (analog gain or digital gain) and a fluorescence evaluation value (analog gain or digital gain) have a constant deviation D.

Specifically, it is assumed a case where the intensity of the NR processing executed on the normal light image is set to an intensity WLIS1 according to a normal light evaluation value WLIG1 in the first image processing. In this case, in the second image processing, the intensity of the NR processing executed on the fluorescence image is set to an intensity IRS1 according to a fluorescence evaluation value IRG1 obtained by adding the deviation D to the normal light evaluation value WLIG1.

Similarly, it is assumed a case where the intensity of the NR processing executed on the normal light image is set to an intensity WLIS2 according to a normal light evaluation value WLIG2 in the first image processing. In this case, in the second image processing, the intensity of the NR processing executed on the fluorescence image is set to an intensity IRS2 according to a fluorescence evaluation value IRG2 obtained by adding the deviation D to the normal light evaluation value WLIG2.

Similarly, it is assumed a case where the intensity of the NR processing executed on the normal light image is set to an intensity WLIS3 according to a normal light evaluation value WLIG3 in the first image processing. In this case, in the second image processing, the intensity of the NR processing executed on the fluorescence image is set to an intensity IRS3 according to a fluorescence evaluation value IRG3 obtained by adding the deviation D to the normal light evaluation value WLIG3.

Incidentally, the effect of removing noise increases as the intensity of the NR processing is higher.

In Steps S18 to S20 according to the above-described embodiment, the control device 9 executes the detection processing on the normal light image after having been subjected to the first image processing in Step S16, and calculates the normal light evaluation value based on the detection information obtained by the detection processing. Further, the control device 9 calculates the fluorescence evaluation value from the normal light evaluation value. However, the present disclosure is not limited thereto, and the following processing may be adopted.

That is, the control device 9 executes detection processing on the fluorescence image after having been subjected to the second image processing in Step S16 and calculates the fluorescence evaluation value based on the detection information obtained by the detection processing. Further, the control device 9 calculates the normal light evaluation value from the fluorescence evaluation value.

Although the number of image processors is four in the above-described embodiment, but the number may be other values without being limited thereto. For example, when a normal light image having the number of pixels of 8K is processed in the normal observation mode, it is necessary to provide sixteen image processors in a case of using an image processor in which the maximum amount of data that may be processed is the amount of data of the full HD image similarly to the above-described embodiment.

Although the imaging element 522 is configured using the imaging element that generates the image having the number of pixels of 4K in the above-described embodiment, an imaging element that generates an image having another number of pixels may be used without being limited thereto.

In the above-described embodiment, a configuration in which only the fluorescence observation mode is provided without providing the normal observation mode may be adopted.

Although the light in the first wavelength band is the white light and the excitation light in the second wavelength band is the near-infrared excitation light in the above-described embodiment, but the present disclosure is not limited thereto. As the first and second light sources 31 and 32 having different first and second wavelength bands, other configurations may be adopted as long as the first light source 31 emits light in the first wavelength band and the second light source 32 emits light in the second wavelength band different from the first wavelength band. At this time, the first and second wavelength bands may be partially overlapping bands or may be completely non-overlapping bands. In addition, the first light source 31 may emit narrow band light.

Meanwhile, photodynamic diagnosis (PDD), which is one of cancer diagnostic methods for detecting cancer cells, is conventionally known.

In the photodynamic diagnosis, a photosensitive substance such as 5-aminolevulinic acid (hereinafter referred to as 5-ALA) is used. The 5-ALA is a natural amino acid originally included in a living body of an animal or a plant. This 5-ALA is taken into a cell after administration into the body and biosynthesized into protoporphyrin in a mitochondrion. Further, the protoporphyrin is excessively accumulated in a cancer cell. In addition, protoporphyrin excessively accumulated in the cancer cell has photoactivity. Therefore, when excited with excitation light (for example, blue visible light in a wavelength band of 375 nm to 445 nm), the protoporphyrin emits fluorescence (for example, red fluorescence in a wavelength band of 600 nm to 740 nm). A cancer diagnosis method in which a photosensitive substance is used to make the cancer cell to fluoresce in this manner is called photodynamic diagnosis.

Further, in the above-described embodiment, the first light source 31 may be configured using an LED that emits white light and the second light source 32 may be configured using a semiconductor laser that emits excitation light that excites protoporphyrin (for example, blue visible light in a wavelength band of 375 nm to 445 nm). Even in the case configured in this manner, the same effect as that of the above-described embodiment may be achieved.

Although the first and second periods are set to be alternately repeated in the fluorescence observation mode in the above-described embodiment, the present disclosure is not limited thereto, and may be configured such that at least one of the first and second periods are continuous and a frequency ratio between the first and second periods is a ratio other than 1:1.

Although the medical image processing apparatus is mounted on the medical observation system 1 in which the insertion unit 2 is configured using the rigid endoscope in the above-described embodiment, but the present disclosure is not limited thereto. For example, the medical image processing apparatus may be mounted on a medical observation system in which the insertion unit 2 is configured using a flexible endoscope. In addition, the medical image processing apparatus may be mounted on a medical observation system such as a surgical microscope (see, for example, JP 2016-42981 A) that magnifies a predetermined visual field area inside a subject (inside a living body) or on a surface of the subject (a surface of the living body) for observation.

In the above-described embodiment, a partial configuration of the camera head 5 and a partial configuration of the control device 9 may be provided in the connector CN1 or the connector CN2, for example.

According to the medical image processing apparatus and the medical observation system, an image suitable for observation may be generated.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical image processing apparatus comprising:
at least one processor configured to:
acquire a first captured image obtained by capturing light from an observation target irradiated with light in a first wavelength band, the observation target emitting fluorescence when irradiated with excitation light in a second wavelength band different from the first wavelength band;
acquire a second captured image obtained by capturing the fluorescence from the observation target irradiated with the excitation light;
execute image processing on the first captured image; and
execute image processing including blurring processing of blurring an image on the second captured image.

2. The medical image processing apparatus according to claim 1, wherein the at least one processor is further configured to:
calculate an evaluation value used for control of brightness of the second captured image based on one of the first captured image and the second captured image; and
change an intensity of the blurring processing based on the evaluation value.

3. The medical image processing apparatus according to claim 2, wherein the at least one processor is further configured to:
set the intensity of the blurring processing to a first intensity when the evaluation value is a first evaluation value; and
set the intensity of the blurring processing to a second intensity, which is higher than the first intensity, when the evaluation value is a second evaluation value which is a value for increasing the brightness of the second captured image more than the first evaluation value.

4. The medical image processing apparatus according to claim 1, wherein the at least one processor is further configured to execute the image processing including image enhancement processing of enhancing an image on the first captured image.

5. The medical image processing apparatus according to claim 4, wherein the at least one processor is further configured to:
calculate an evaluation value used for control of brightness of the first captured image based on one of the first captured image and the second captured image; and
change an intensity of the image enhancement processing according to the evaluation value.

6. The medical image processing apparatus according to claim 5, wherein the at least one processor is further configured to:
set the intensity of the image enhancement processing to a third intensity when the evaluation value is a third evaluation value; and
set the intensity of the image enhancement processing to a fourth intensity, which is lower than the third intensity, when the evaluation value is a fourth evaluation value which is a value for increasing the brightness of the first captured image more than the third evaluation value.

7. The medical image processing apparatus according to claim 1, wherein the at least one processor is further configured to switch between a first observation mode and a second observation mode,
wherein the medical image processing apparatus further comprises a memory configured to temporarily store an image,
wherein the at least one processor is further configured to control writing of an image to the memory and reading of an image from the memory,
wherein the at least one processor includes a plurality of image processors configured to execute image processing in parallel on each input image,
wherein the at least one processor is further configured to:
write the first captured image to a first memory area in the memory, read a plurality of divided images, obtained by dividing the first captured image into the images, a number of which corresponds to a number of a plurality of image processors among the at least one process, respectively from a plurality of divided areas in the first memory area in which the plurality of divided images have been written and output the plurality of divided images to the plurality of image processors in the first observation mode; and
write the first captured image and the second captured image to a second memory area and a third memory area having a similar memory capacity to the divided area in the memory, respectively, read the first captured image and the second captured image respectively from the second memory area and the third memory area and output the first captured image and the second captured image to a first image processor and a second image processor, respectively, among the plurality of the image processors in the second observation mode.

8. The medical image processing apparatus according to claim 7, wherein
the first captured image of which a total number of pixels is a first number of pixels is written to the first memory area in the memory in the first observation mode, and
the first captured image and the second captured image after having been subjected to thinning processing, which makes the total number of pixels a second number of pixels which is equal to or smaller than 1/N of the first number of pixels when the number of image processors is N, are written to the second memory area and the third memory area in the memory, respectively, in the second observation mode.

9. A medical observation system comprising:
a light source configured to emit light in a first wavelength band and excitation light in a second wavelength band different from the first wavelength band;
a camera configured to capture light from an observation target, the observation target emitting fluorescence when irradiated with the excitation light and being irradiated with the light in the first wavelength band, to generate a first captured image and capture the fluorescence from the observation target irradiated with the excitation light to generate a second captured image; and
the medical image processing apparatus according to claim 1 configured to process the first captured image and the second captured image.

10. The medical observation system according to claim 9, further comprising at least one processor configured to:
calculate an evaluation value used for control of brightness of the second captured image based on one of the first captured image and the second captured image; and
change an intensity of the blurring processing based on the evaluation value.

11. The medical observation system according to claim 10, wherein the at least one processor is further configured to:
set the intensity of the blurring processing to a first intensity when the evaluation value is a first evaluation value; and
set the intensity of the blurring processing to a second intensity, which is higher than the first intensity, when the evaluation value is a second evaluation value which is a value for increasing the brightness of the second captured image more than the first evaluation value.

12. The medical observation system according to claim 9, wherein the at least one processor is further configured to execute the image processing including image enhancement processing of enhancing an image on the first captured image.

13. A method for processing an image comprising:
acquiring a first captured image obtained by capturing light from an observation target irradiated with light in a first wavelength band, the observation target emitting fluorescence when irradiated with excitation light in a second wavelength band different from the first wavelength band;
acquiring a second captured image obtained by capturing the fluorescence from the observation target irradiated with the excitation light;
executing image processing on the first captured image; and
executing image processing including blurring processing of blurring an image on the second captured image.

14. The method according to claim 13, further comprising:
calculating an evaluation value used for control of brightness of the second captured image based on one of the first captured image and the second captured image; and
changing an intensity of the blurring processing based on the evaluation value.

15. The method according to claim 14, further comprising:
setting the intensity of the blurring processing to a first intensity when the evaluation value is a first evaluation value; and
setting the intensity of the blurring processing to a second intensity, which is higher than the first intensity, when the evaluation value is a second evaluation value which is a value for increasing the brightness of the second captured image more than the first evaluation value.

16. The method according to claim 13, further comprising executing the image processing including image enhancement processing of enhancing an image on the first captured image.

17. The method according to claim 16, further comprising:
calculating an evaluation value used for control of brightness of the first captured image based on one of the first captured image and the second captured image; and
changing an intensity of the image enhancement processing according to the evaluation value.

18. The method according to claim 17, further comprising:
setting the intensity of the image enhancement processing to a third intensity when the evaluation value is a third evaluation value; and
setting the intensity of the image enhancement processing to a fourth intensity, which is lower than the third intensity, when the evaluation value is a fourth evaluation value which is a value for increasing the brightness of the first captured image more than the third evaluation value.

19. The method according to claim 13, further comprising:
switching between a first observation mode and a second observation mode;
executing image processing in parallel on each input image with a plurality of image processors;
writing the first captured image to a first memory area in a memory;
reading a plurality of divided images, obtained by dividing the first captured image into the images, a number of which corresponds to a number of a plurality of image processors, respectively from a plurality of divided areas in the first memory area in which the plurality of divided images have been written and output the plurality of divided images to the plurality of image processors in the first observation mode;
writing the first captured image and the second captured image to a second memory area and a third memory area having a similar memory capacity to the divided area in the memory, respectively;
reading the first captured image and the second captured image respectively from the second memory area and the third memory area; and
outputting the first captured image and the second captured image to a first image processor and a second image processor, respectively, among the plurality of the image processors in the second observation mode.

20. The method according to claim 19, further comprising:
writing the first captured image of which a total number of pixels is a first number of pixels to the first memory area in the memory in the first observation mode; and
writing the first captured image and the second captured image after having been subjected to thinning processing, which makes the total number of pixels a second number of pixels which is equal to or smaller than UN of the first number of pixels when the number of image processors is N, to the second memory area and the third memory area in the memory, respectively, in the second observation mode.

* * * * *